United States Patent
Liu et al.

(10) Patent No.: US 7,239,121 B2
(45) Date of Patent: Jul. 3, 2007

(54) QUANTATIVE EXTRACTION OF MICRO PARTICLES FROM METALLIC DISK SPACER RINGS

(75) Inventors: Shaoyong Liu, Singapore (SG); Kor Seng Kelvin Ang, Singapore (SG); Sivalingam Marimuthu, Singapore (SG); Jingjing Zhang, Singapore (SG); Yi Zhao Yao, Singapore (SG)

(73) Assignee: Hitachi Global Storage Technologies Netherlands B.V., Amsterdam (NL)

( * ) Notice: Subject to any disclaimer, the term of this patent is extended or adjusted under 35 U.S.C. 154(b) by 0 days.

(21) Appl. No.: 11/078,592

(22) Filed: Mar. 11, 2005

(65) Prior Publication Data

US 2006/0202670 A1    Sep. 14, 2006

(51) Int. Cl.
G01N 27/00    (2006.01)
B23H 3/00    (2006.01)

(52) U.S. Cl. .................... 324/71.4; 204/224 M; 204/242; 205/645; 205/674

(58) Field of Classification Search ................ 324/71.4; 204/640, 645
See application file for complete search history.

(56) References Cited

U.S. PATENT DOCUMENTS

| | | | | |
|---|---|---|---|---|
| 4,349,423 A | * | 9/1982 | Nutzel et al. | ............... 205/717 |
| 4,668,355 A | * | 5/1987 | Lin | ............... 205/216 |
| 4,886,552 A | | 12/1989 | Jaworowski et al. | |
| 5,519,330 A | * | 5/1996 | Yamauchi et al. | .......... 324/700 |
| 5,724,208 A | | 3/1998 | Yahata | |
| 5,768,052 A | | 6/1998 | Smith | |
| 5,907,457 A | * | 5/1999 | Kudo et al. | ............... 360/246.2 |
| 6,776,172 B2 | * | 8/2004 | Okumura | ............... 134/22.11 |
| 2003/0175471 A1 | | 9/2003 | Kaneko | |
| 2003/0179494 A1 | | 9/2003 | Kaneko | |
| 2003/0223280 A1 | | 12/2003 | Okumura et al. | |

FOREIGN PATENT DOCUMENTS

| | | |
|---|---|---|
| JP | 4082066 | 3/1992 |
| JP | 10074350 | 3/1998 |
| JP | 10106202 | 4/1998 |
| JP | 2001283550 | 10/2001 |
| JP | 2002230933 | 8/2002 |
| JP | 2003059224 | 2/2003 |
| JP | 2003308672 | 10/2003 |

* cited by examiner

Primary Examiner—Andrew H. Hirshfeld
Assistant Examiner—John Zhu

(57) ABSTRACT

Embodiments of the present invention include a method for quantitatively detecting embedded particles of a disk spacer ring comprising. The method includes dissolving a layer of a disk spacer ring into a liquid solution, the disk spacer ring layer comprising embedded particles. The method further includes filtering the solution to capture the embedded particles. The method further includes counting the particles.

13 Claims, 3 Drawing Sheets

300

```
┌─────────────────────────────────────────────┐
│ Dissolving a layer of a disk spacer ring into a │
│ liquid solution, the disk spacer ring layer     │
│ comprising embedded particles                   │
│ 301                                             │
└─────────────────────────────────────────────┘
                      │
                      ▼
┌─────────────────────────────────────────────┐
│ Filtering the solution to capture the           │
│ embedded particles                              │
│ 303                                             │
└─────────────────────────────────────────────┘
                      │
                      ▼
┌─────────────────────────────────────────────┐
│ Quantifying the particles                       │
│ 305                                             │
└─────────────────────────────────────────────┘
```

FIG. 3

QUANTATIVE EXTRACTION OF MICRO PARTICLES FROM METALLIC DISK SPACER RINGS

FIELD OF THE INVENTION

The present invention relates to the manufacture and handling of magnetic read/write work pieces. More specifically, embodiments of the present invention relate to extracting micro particles from metallic disk spacer rings.

BACKGROUND OF THE INVENTION

Conventionally, a data access and storage system comprises one or more storage devices that store data on a magnetic or optical storage media. One example of a magnetic storage device is a hard disk drive. Another example of a magnetic storage device is a direct access storage device. Each of these devices can comprise one or more disks and a disk controller to manage operations on each of the disks. Many times, spacer rings are used to separate the disks.

One problem with conventional spacer rings is that they sometimes create dust (particles) that can contaminate the disk drive and can disturb long-term reliability of the device. It is suspected that manufacture processing of the disk spacers is a leading cause of the dust contamination. Particularly, the disk spacers are polished with an abrasive (e.g., silicon carbide) material that is sometimes embedded and adhered to the disk spacer.

Heat generated during the operation of the device causes thermal expansion of the spacer ring. The spacer ring expands at a different rate than the embedded particles, which can cause the particles to dislodge and fall off the spacer ring. The particles eventually cause scratching of the disks and the read/write components.

The detection of the particles has become an important concern. The ability to detect them quantitatively facilitates particulate contamination control of incoming spacer rings from suppliers and guide the spacer ring suppliers

SUMMARY OF THE INVENTION

Embodiments of the present invention include a method for quantitatively detecting embedded particles of a disk spacer ring comprising. The method includes dissolving a layer of a disk spacer ring into a liquid solution, the disk spacer ring layer comprising embedded particles. The method further includes filtering the solution to capture the embedded particles. The method further includes counting the particles.

BRIEF DESCRIPTION OF THE DRAWINGS

The above and other objects and advantages of the present invention will be more readily appreciated from the following detailed description when read in conjunction with the accompanying drawings, wherein:

FIG. 3 is a flow diagram of an exemplary method of quantifying embedded particles of a disk spacer ring in accordance with embodiments of the present invention.

DETAILED DESCRIPTION OF THE INVENTION

Figure 1:
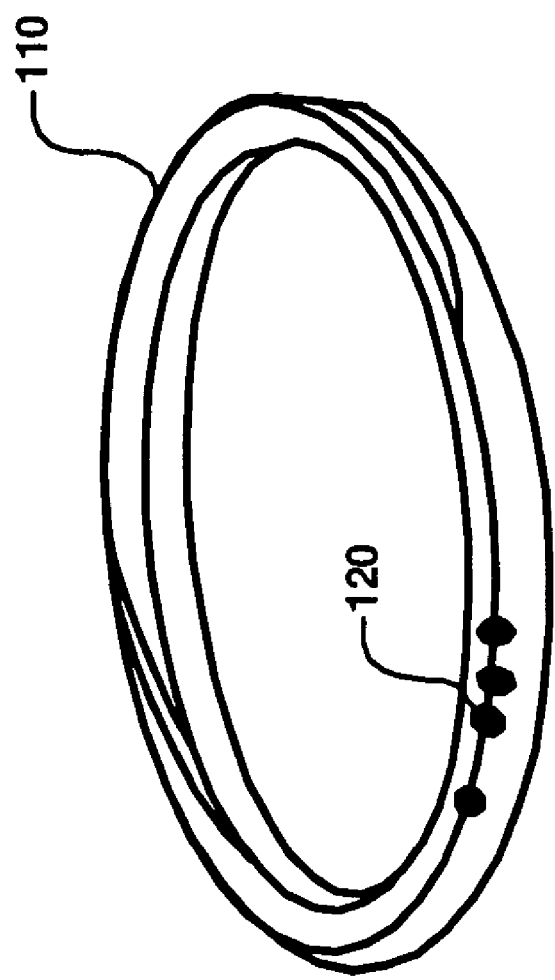
FIG. 1 is an illustration of an exemplary disk spacer ring comprising embedded particles in accordance with embodiments of the present invention.

Reference will now be made in detail to embodiments of the present invention, a system and method for striping data, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims.

Furthermore, in the following detailed description of the present invention, numerous specific details are set forth in order to provide a thorough understanding of the present invention. However, it will be recognized by one of ordinary skill in the art that the present invention may be practiced without these specific details. In other instances, well known methods, procedures, components, and circuits have not been described in detail as not to unnecessarily obscure aspects of the present invention.

The presence of silicon carbide (SiC) micro particles in the disk spacer ring used in a hard disk drive (HDD) contributes extensively to reliability issues. These very hard SiC particles come from the grinding process (a SiC grinding stone or SiC slurry used for lapping) during the thinning of the spacer ring at a supplier's manufacturing site. During the operation of the HDD, heat is induced and causes the spacer ring to expand. Unfortunately, the thermal expansion of the spacer ring is usually different from the SiC particles, which causes embedded SiC particles to come loose from the spacer ring. The SiC particles eventually fall onto the HDD disk surface causing scratching of the disk surface and the read/write devices of the HDD.

The detection of the SiC particles is an important concern. Embodiments of the present invention provide a novel method and system for quantitatively identifying the particles that facilitates SiC contamination control of disk spacer rings. The quantitative identification of the SiC particles can be used to guide disk spacer ring suppliers to improve their grinding processes to reduce SiC particulate contamination, thus improving overall device functionality and reliability.

Direct observation of SiC on a spacer ring by a scanning electron microscope (SEM) can only be used as a qualitative method. It is not always practical to quantify the amount of SiC particles using the SEM as the observation of the total surface area of one spacer ring may take up to a few days. Observing for SiC particles at the chamfer area also proves to be a challenge by using the SEM due to the topography of the spacer ring chamfer area.

Embodiments of the present invention use an electrolysis process to dissolve a layer of a disk spacer ring at the anode, completely exposing embedded SiC particles, which allow the originally partially and fully embedded particles to fall into a solution. The electrolysis solution is then filtered through a suitable membrane and the particles are collected and counted. In one embodiment of the invention, a SEM is used to count the particles filtered by the membrane.

The thinning of the spacer ring during the electrolysis process is a mild and gradual process, which is easy to control. Controlling parameters include solution concentration, time, voltage and current. The exemplary process does not lead to any environmental pollution as the solution required is of little volume and is low in concentration. The exemplary process can be implemented in HDD manufacturing and spacer ring manufacturing. The method extracts the embedded particles of a spacer ring accurately, effectively and quantitatively.

FIG. 1 is an illustration of an exemplary disk spacer ring 110 comprising embedded particles 120. In one embodiment of the invention, the disk spacer ring 110 is metallic and comprises iron, chromium, titanium, aluminum, or any other metal. In one embodiment of the invention, the embedded particles 120 are SiC, however, the particles 120 could be any byproduct of a polishing process done on the spacer ring 110 or any foreign embedded particles. In one embodiment of the invention, the particles 120 are fully embedded or partially embedded in the spacer ring 110.

Figure 2:
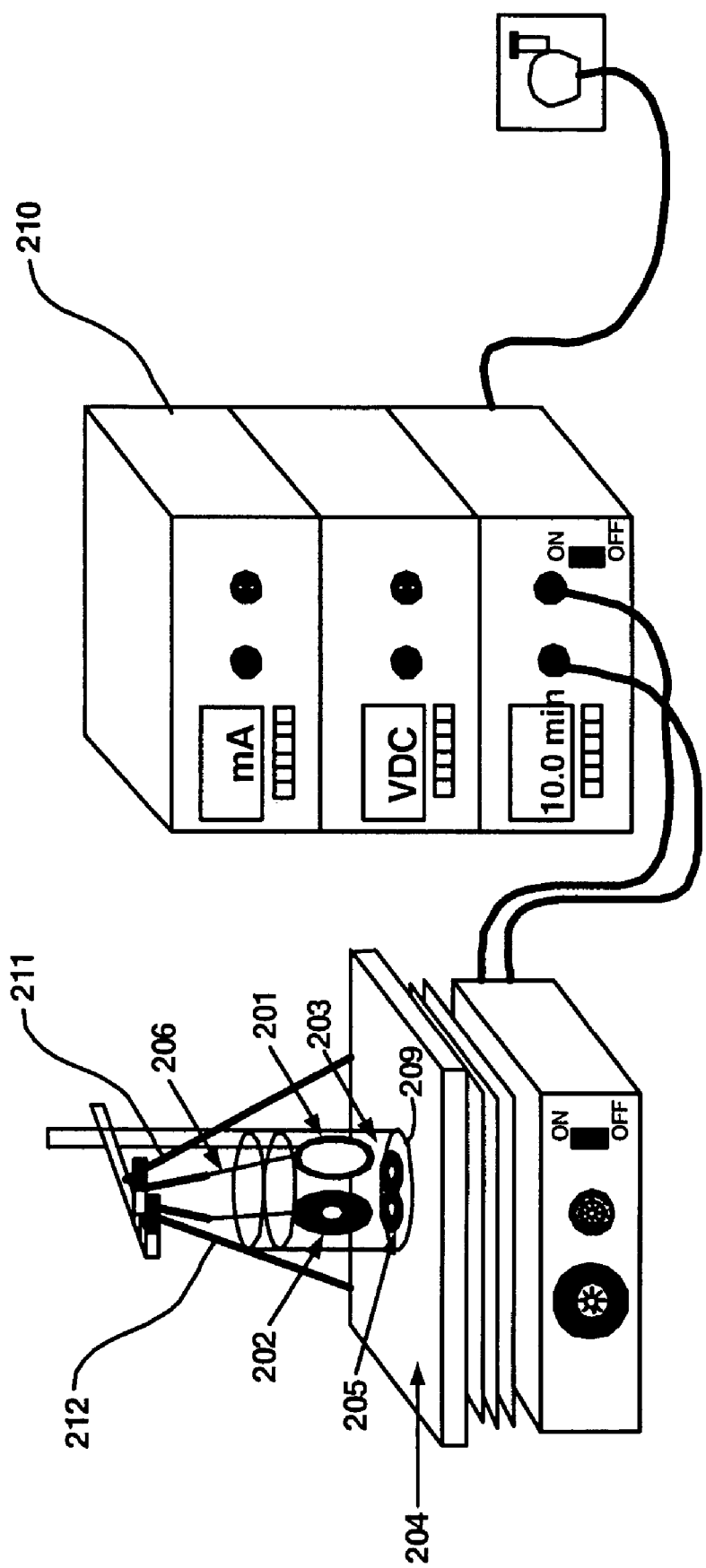
FIG. 2 is an illustration of an exemplary system for extracting embedded particles of a spacer ring using an electrolysis process in accordance with embodiments of the present invention.

FIG. 2 is an illustration of an exemplary system for extracting embedded particles of a disk spacer ring in accordance with embodiments of the present invention. The spacer ring undergoes electrolysis whereby the spacer ring is made the anode 201. A more inert metallic material (e.g., stainless steel, platinum, etc.) can be used as the cathode 202. Both the anode 201 and the cathode 202 are immersed in a vessel 209 containing a liquid solution 203. In one embodiment of the invention, the vessel 209 has a capacity of substantially 100 ml. However, the vessel 209 can be any shape or capacity. In one embodiment of the invention, the liquid solution comprises an acid. For example, the liquid solution can comprise nitric acid, hydrochloric acid or sulphuric acid. In one embodiment of the invention, the volume of the liquid solution is substantially 50 ml and the concentration of the acid is substantially 0.1M.

A power supply 210 supplies a current and voltage for the electrolysis process. A positive terminal 211 is electrically coupled to the anode 201 (spacer ring 110) and a negative terminal 212 is electrically coupled to the cathode 202. In one embodiment of the invention, a voltage of substantially 2.88V and a current of 1 mA are supplied to drive the electrolysis process. In one embodiment of the invention, a platinum wire 206 is used to couple the anode 201 and the cathode 202 to the power supply 210. In one embodiment of the invention, a magnetic stirrer 205 and magnetic plate 204 are used to stir the liquid solution 203.

The reaction can be expressed as follows:

Anode: $M(s) - ne === M^{n+}(aq)$ 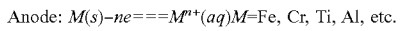 M=Fe, Cr, Ti, Al, etc.

Cathode: $2H^+ + 2e === H_2(g)$ 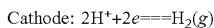

After a predetermined period of time (e.g., 30 minutes), the liquid solution is filtered and the filtered particles are counted. The number of particles can be used to quantitatively determine the contamination of the spacer ring due to embedded particles. The system can be used to quantitatively measure the number of particles in other spacer rings made of different materials such as titanium, aluminum, chromium, etc.

TABLE 1

Working conditions for electrolysis at different concentrations of solution.

| Concentration of $H_2SO_4$ (mol/L) | Working Voltage (V) |
| --- | --- |
| 0.5 | 2.65 |
| 0.2 | 2.8 |
| 0.1 | 2.88 |
| 0.05 | 3.14 |

From Table 1, it is observed that as the concentration of the solution decreases, the amount of voltage passing through the solution increases.

Table 2 shows the data for extraction time against the thickness reduction of a spacer ring.

| Extraction Time (min) | Thickness Reduction (μm) using 0.05M $H_2SO_4$ | Thickness Reduction (μm) using 0.1M $H_2SO_4$ | Thickness Reduction (μm) using 0.2M $H_2SO$ |
| --- | --- | --- | --- |
| 0 | 0 | 0 | 0 |
| 15 | 0.3 | 1.0 | 0.3 |
| 30 | 1.7 | 3.0 | 2.0 |
| 60 | 2.3 | 4.0 | 4.0 |

As all of the particle sizes are in micron or sub-microns from Table 2, the results show that a 30 min extraction is sufficient to remove all particles from the spacer ring at different acid concentrations.

TABLE 3

Working conditions for electrolysis at different concentrations of HCL solution.

| Concentration of HCL (mol/L) | Working Voltage (V) |
| --- | --- |
| 1.0 | 2.60 |
| 0.4 | 2.78 |
| 0.2 | 2.90 |
| 0.1 | 3.05 |

FIG. 3 is a flow diagram of an exemplary process 300 for extracting embedded particles from a disk spacer ring in accordance with embodiments of the present invention.

At step 301, process 300 includes dissolving a layer of a disk spacer ring into a liquid solution, the disk spacer ring layer comprising embedded particles. In one embodiment of the invention, the layer is dissolved with the electrolysis process described above.

In one embodiment of the invention, the disk spacer ring is made the anode of the electrolysis process. In one embodiment of the invention, the liquid solution comprises nitric acid, hydrochloric acid or sulphuric acid or any other acid suitable for an electrolysis process.

In one embodiment of the invention, an inert metal is made the cathode of the electrolysis process. In one embodiment of the invention, the cathode comprises stainless steel, chromium, titanium, or aluminum or any other suitable inert metal that can be used for the electrolysis process.

In one embodiment of the invention, the layer removed from the disk spacer ring and dissolved in the solution is substantially 2 microns in thickness. In one embodiment of the invention, the voltage used for the electrolysis process is equal to or less than 3 volts and the current is equal to or less than 1 mA. In one embodiment of the invention, the particles embedded in the disk spacer ring comprise silicon carbide or any other material used to grind or polish the disk spacer ring.

At step 303, process 300 includes filtering the solution to capture the embedded particles. In one embodiment of the invention, the solution is passed through a membrane to capture the particles. In one embodiment of the invention, the particles are 1 micron in size or less.

At step 305, process 300 includes quantifying the particles. In one embodiment of the invention, a scanning electron microscope is used to quantify the particles. It is appreciated that other methods or systems can be used to quantify the particles filtered from the electrolysis solution.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and it's practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A method for quantitatively detecting embedded particles of a disk spacer ring comprising:
   dissolving an outer layer of said disk spacer ring into a liquid solution, said disk spacer ring outer layer comprising embedded non-metallic particles, wherein said embedded particles are not dissolved in said liquid solution and wherein an inner layer of said disk spacer ring is not dissolved;
   filtering said solution to capture said embedded particles; and
   quantifying said particles.

2. The method of claim 1 wherein said layer of said disk spacer is dissolved by electrolysis.

3. The method of claim 2 wherein said disk spacer ring is an anode of an electrical-chemical reaction.

4. The method of claim 1 wherein said liquid solution comprises nitric acid, hydrochloric acid or sulphuric acid.

5. The method of claim 1 wherein said disk spacer ring comprises stainless steel, titanium, chromium, iron, or aluminum.

6. The method of claim 1 wherein said layer of said disk spacer ring is less than 2 microns in thickness.

7. The method of claim 1 further comprising:
   applying a positive voltage to said disk spacer ring applying a negative voltage to a sacrificial cathode.

8. The method of claim 7 wherein said positive voltage is less than 3 volts.

9. The method of claim 1 wherein said particles comprise silicon carbide.

10. The method of claim 1 wherein said counting comprises using a scanning electron microscope to quantify said particles.

11. A method for quantitatively detecting embedded non-metallic particles of a disk spacer ring comprising:
    electro-chemically removing an outer layer of said disk spacer ring, said outer layer of said disk spacer ring comprising non-metallic embedded particles, wherein said particles are not dissolved and wherein an inner layer of said disk spacer ring is not dissolved;
    isolating said embedded particles;
    counting said embedded particles.

12. The method of claim 11 wherein said counting comprises quantifying said embedded particles with a scanning electron microscope.

13. The method of claim 11 wherein said isolating comprises filtering an acid solution comprising said embedded particles.

* * * * *